United States Patent
Lill et al.

(10) Patent No.: US 12,043,642 B2
(45) Date of Patent: Jul. 23, 2024

(54) PROCESS FOR THE PURIFICATION OF OLIGONUCLEOTIDES

(71) Applicant: Hoffmann-La Roche Inc., Little Falls, NJ (US)

(72) Inventors: Joerg Lill, Aarau (CH); Filippo Sladojevich, Rheinfelden (CH)

(73) Assignee: GENENTECH, INC., South San Francisco, CA (US)

( * ) Notice: Subject to any disclaimer, the term of this patent is extended or adjusted under 35 U.S.C. 154(b) by 649 days.

(21) Appl. No.: 17/236,501

(22) Filed: Apr. 21, 2021

(65) Prior Publication Data

US 2021/0347800 A1  Nov. 11, 2021

Related U.S. Application Data

(63) Continuation of application No. PCT/EP2019/078704, filed on Oct. 22, 2019.

(30) Foreign Application Priority Data

Oct. 24, 2018 (EP) ................................. 18202335

(51) Int. Cl.
*C07H 1/06* (2006.01)
*B01D 69/02* (2006.01)
*C07H 21/00* (2006.01)

(52) U.S. Cl.
CPC ............... *C07H 1/06* (2013.01); *B01D 69/02* (2013.01); *C07H 21/00* (2013.01); *B01D 2325/20* (2013.01)

(58) Field of Classification Search
CPC ............ C07H 1/06; C07H 21/00; B01D 69/02
See application file for complete search history.

(56) References Cited

U.S. PATENT DOCUMENTS

| | | | |
|---|---|---|---|
| 2004/0044195 A1 | 3/2004 | Kwiatkowski et al. | |
| 2009/0087446 A1 | 4/2009 | Vollmer et al. | |
| 2016/0024139 A1* | 1/2016 | Berlanda Scorza ... | C07H 21/00 536/25.4 |
| 2018/0282365 A1 | 10/2018 | Hirai et al. | |

FOREIGN PATENT DOCUMENTS

| | | |
|---|---|---|
| CN | 1155887 A | 7/1997 |
| CN | 1628123 A | 6/2005 |
| CN | 1678618 A | 10/2005 |
| CN | 101137662 A | 3/2008 |
| CN | 102076703 A | 5/2011 |
| CN | 102574912 A | 7/2012 |
| CN | 105283548 A | 1/2016 |
| CN | 106164248 A | 11/2016 |
| CN | 110621700 A | 12/2019 |
| WO | 2004/020449 A1 | 3/2004 |
| WO | 2006/076674 A2 | 7/2006 |
| WO | 2006/108599 A2 | 10/2006 |
| WO | 2008/154639 A2 | 12/2008 |
| WO | 2012/010711 A1 | 1/2012 |
| WO | 2015/061246 A1 | 4/2015 |
| WO | 2015/164773 A1 | 10/2015 |

OTHER PUBLICATIONS

Obika et al., eds., Synthesis of Therapeutic Oligonucleotides, 2018, Springer Nature Singapore Pte Ltd, p. 97-112. (Year: 2018).*
"International Preliminary Report on Patentability—PCT/EP2019/078704" (Report Issuance Date: Apr. 27, 2021; Chapter I),:pp. 1-6 (May 6, 2021).
"International Search Report—PCT/EP2019/078704" (w/Written Opinion),:pp. 1-10 (Jan. 16, 2020).
Krotz et al., "Controlled Detritylation of Antisense Oligonucleotides" Organic Process Research & Development 7(1):47-52 ( 2003).
Egli et al., "Critical Reviews and Perspectives—Chemistry, structure and function of approved oligonucleotide therapuetics" Nucleic Acids Research 51(6):2529-2573 (2023).
Krotz et al., "Controlled Detritrylation of Antisense Oligonucleotides" Organic Process Research & Development 7:47-52 (2003).
Wikipedia, "Oligonucleotide" Wayback Machine Snapshot:3 pages (Aug 16, 2017).
Paredes et al., "Manufacturing of Oligonucleotides" Comprehensive Medicinal Chemistry III 6:233-279 ( 2017).
Scott, "Avoiding Depurination During Trityl-on Purification" Phenomenex, Inc.:8 pages (2007).
F. Hoffmann-La Roche AG, Communication of a notice of opposition dated May 8, 2024 in European Application No. 19789691.3, 46 pages.
Capaldi et al., "Impurities in Oligonucleotide Drug Substances and Drug Products" Nucleic Acid Therapeutics 27(6):309-322 ( 2017).
Wikipedia, "Oligonucleotide synthesis" The Wayback Machine Snapshot:22 pages (Apr 18, 2018).
Sartocube®—Hydrosart® Ultrafilter Cassette Product Sheet, Sartorius Stedim Biotech GmbH:2 pages (Mar 2012).
Schwartz et al., "Introduction to Tangential Flow Filtration for Laboratory and Process Development Applications" PALL Life Sciences:12 pages ( 2003).

* cited by examiner

Primary Examiner — Jonathan S Lau
(74) Attorney, Agent, or Firm — GENENTECH, INC.

(57) ABSTRACT

The invention relates to a new process for the purification of oligonucleotides which comprises the removal of the acid labile 5'hydroxy protecting group at the 5'-O-oligonucleotide terminus of the oligonucleotide by way of tangential flow filtration with an acidic buffer solution. The process requires less steps and allows a higher degree of automation.

13 Claims, No Drawings

Specification includes a Sequence Listing.

PROCESS FOR THE PURIFICATION OF OLIGONUCLEOTIDES

CROSS REFERENCE TO RELATED APPLICATIONS

This application is a continuation of International Application No. PCT/EP2019/078704, filed Oct. 22, 2019, which is claims priority to European Patent Application No. 18202335.8, filed Oct. 24, 2018, which are incorporated herein by reference in its entirety.

SEQUENCE LISTING

This application contains a Sequence Listing which has been submitted electronically in ASCII format and is hereby incorporated by reference in its entirety. Said ASCII copy, created on Feb. 12, 2024, is named P35110-US-SeqListing_replacement.txt and is 543 bytes in size.

The invention relates to a new process for the purification of oligonucleotides which comprises the removal of the acid labile 5'hydroxy protecting group at the 5'-O-oligonucleotide terminus of the oligonucleotide by way of tangential flow filtration with an acidic buffer solution.

The oligonucleotide which is typically prepared via solid phase synthesis, after its cleavage from the resin, still contains a significant amount of impurities. For standard monomers of a 15- to 20-mer length the API purity is at best in the range of 70 to 80%. For chemically modified monomers or for longer sequences the API content is typically even lower.

Selective separation methods have been developed to prepare high purity oligonucleotides which satisfy the specifications of a therapeutic application.

In one method the oligonucleotide, after its cleavage from the resin, is left with the acid labile 5'hydroxy protecting group at the 5'-O-oligonucleotide terminus. The hydrophobicity of this group allows the application of effective chromatography techniques for purification.

It is common strategy that the crude oligonucleotide is passing the following steps (for instance Krotz et al, Organic Process Research & Development 2003, 7, 47-52)
a) reversed phase chromatography
b) concentration and desalting,
c) removal of the acid labile 5'hydroxy protecting group in solution and
d) further concentration and desalting It was found that this known processes require substantial operation time due to the number of single operation steps a) to d).

Object of the invention was to reduce the number of steps, achieve a higher degree of automation and with that reduce overall operation time.

It was found that the object of the invention could be reached with the novel process for the purification of oligonucleotides as outlined above.

The following definitions are set forth to illustrate and define the meaning and scope of the various terms used to describe the invention herein.

The term acid labile 5'hydroxy protecting group is defined as a protecting group which is cleavable with the help of a suitable acid and which has a hydrophobic character.

Typical acid labile 5'hydroxy protecting groups are selected from 4,4'-dimethoxytrityl, 4-methoxytrityl, trityl, 9-phenyl-xanthen-9-, 9-(p-tolyl)-xanthen-9-yl or from tert-butyldimethylsilyl, preferably from 4,4'-dimethoxytrityl, 4-methoxytrityl or trityl or even more preferably from 4,4'-dimethoxytrityl.

The term oligonucleotide as used herein is defined as it is generally understood by the skilled person as a molecule comprising two or more covalently linked nucleotides. For use as a therapeutically valuable oligonucleotide, oligonucleotides are typically synthesized as 10 to 40 nucleotides, preferably 10 to 25 nucleotides in length.

The oligonucleotides may consist of optionally modified DNA, RNA or LNA nucleoside monomers or combinations thereof.

The LNA nucleoside monomers are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

Optionally modified as used herein refers to nucleosides modified as compared to the equivalent DNA, RNA or LNA nucleoside by the introduction of one or more modifications of the sugar moiety or the nucleo base moiety. In a preferred embodiment the modified nucleoside comprises a modified sugar moiety, and may for example comprise one or more 2' substituted nucleosides and/or one or more LNA nucleosides. The term modified nucleoside may also be used herein interchangeably with the term "nucleoside analogue" or modified "units" or modified "monomers".

The DNA, RNA or LNA nucleosides are as a rule linked by a phosphodiester (P=O) and/or a phosphorothioate (P=S) internucleoside linkage which covalently couples two nucleosides together.

Accordingly, in some oligonucleotides all internucleoside linkages may consist of a phosphodiester (P=O), in other oligonucleotides all internucleoside linkages may consist of a phosphorothioate (P=S) or in still other oligonucleotides the sequence of internucleoside linkages vary and comprise both phosphodiester (P=O) and phosphorothioate (P=S) internucleoside.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are described with capital letters A, T, G and $^{Me}C$ (5-methyl cytosine) for LNA nucleoside and with small letters a, t, g, c and $^{Me}C$ for DNA nucleosides. Modified nucleobases include but are not limited to nucleobases carrying protecting groups such as tert.butylphenoxyacetyl, phenoxyacetyl, benzoyl, acetyl, isobutyryl or dimethylformamidino (see Wikipedia, Phosphoramidit-Synthese, https://de.wikipedia.org/wild/Phosphoramidit-Synthese of Mar. 24, 2016).

Preferably the oligonucleotide consists of optionally modified DNA, RNA or LNA nucleoside monomers or combinations thereof and is 10 to 40, preferably 10 to 25 nucleotides in length.

The principles of the oligonucleotide synthesis are well known in the art (see e.g. Oligonucleotide synthesis; Wikipedia, the free encyclopedia; https://en.wikipedia.org/wiki/Oligonucleotide synthesis, of Mar. 15, 2016).

Larger scale oligonucleotide synthesis nowadays is carried automatically using computer controlled synthesizers.

As a rule, oligonucleotide synthesis is a solid-phase synthesis, wherein the oligonucleotide being assembled is covalently bound, via its 3'-terminal hydroxy group, to a solid support material and remains attached to it over the entire course of the chain assembly. Suitable supports are the commercial available macroporous polystyrene supports like the Primer support 5G from GE Healthcare or the NittoPhase®HL support from Kinovate.

The oligonucleotide synthesis in principle is a stepwise addition of nucleotide residues to the 5'-terminus of the growing chain until the desired sequence is assembled.

As a rule, each addition is referred to as a synthetic cycle and in principle consists of the chemical reactions $a_1$) de-blocking the protected hydroxyl group on the solid support, $a_2$) coupling the first nucleoside as activated phosphoramidite with the free hydroxyl group on the solid support, $a_3$) oxidizing or sulfurizing the respective P-linked nucleoside to form the respective phosphodiester (P=O) or the respective phosphorothioate (P=S);

$a_4$) optionally, capping any unreacted hydroxyl groups on the solid support;

$a_5$) de-blocking the 5' hydroxyl group of the first nucleoside attached to the solid support;

$a_6$) coupling the second nucleoside as activated phosphoramidite to form the respective P-linked dimer;

$a_7$) oxidizing or sulfurizing the respective P-linked dinucleoside to form the respective phosphodiester (P=O) or the respective phosphorothioate (P=S);

$a_8$) optionally, capping any unreacted 5' hydroxyl groups;

$a_9$) repeating the previous steps $a_5$ to $a_8$ until the desired sequence is assembled.

The subsequent cleavage from the resin can be performed with concentrated aqueous ammonia. The protecting groups on the phosphate and the nucleotide base are also removed within this cleavage procedure.

The crude oligonucleotide after the cleavage is left with the acid labile 5'hydroxy protecting group at the 5'-O-oligonucleotide terminus.

The process is characterized by the removal of the acid labile 5'hydroxy protecting group at the 5'-O-oligonucleotide terminus of the oligonucleotide by way of tangential flow filtration with an acidic buffer solution.

The term acid labile 5'hydroxy protecting group is defined as above as a protecting group which is cleavable with the help of a suitable acid and which has a hydrophobic character.

Typical acid labile 5'hydroxy protecting groups are selected from 4,4'-dimethoxytrityl, 4-methoxytrityl, trityl, 9-phenyl-xanthen-9-, 9-(p-tolyl)-xanthen-9-yl or from tert-butyldimethylsilyl, preferably from 4,4'-dimethoxytrityl, 4-methoxytrityl or trityl or even more preferably from 4,4'-dimethoxytrityl (DMT).

An acidic buffer is an aqueous solution of a weak acid and its conjugate base which is acidified with a protonic acid to bring the pH in the desired range.

Typical acidic buffers are acetate or citrate buffers which are composed of acetic acid or citric acid as weak acid and its sodium salt as conjugate base.

The protonic acid used for acidification of the acidic buffer can be selected from aqueous mineral acids, such as from hydrochloric acid, phosphoric acid, sulfuric acid or nitric acid, but usually from aqueous hydrochloric acid.

The desired pH ranges ideally between 2 to 6, preferably between of 2.5 to 4.0, even more preferably between 2.8 and 3.5.

The acidic buffer solution may also contain a polar protic or a polar aprotic organic solvent in an amount of 5% (V) to 50% (V), preferably in an amount of 20% (V) to 40% (V).

Suitable polar protic solvents are the primary aliphatic alcohols such as methanol, ethanol or i-propanol, preferably ethanol.

Suitable polar aprotic solvents are acetonitrile, dimethylsulfoxide or N-methyl-2-pyrrolidone, but preferably acetonitrile.

In a preferred embodiment the acid buffer is an acetate buffer which is acidified with aqueous hydrochloric acid to a pH in the range of 2.8. to 3.5 and subsequently diluted with ethanol to form a buffer solution containing 35% (V) to 45% (V) ethanol.

The acetate concentration can be selected in the range of 10 mmol/l to 1 mol/l, preferably in the range of 50 mmol/l to 250 mmol/l.

The tangential flow filtration is characterized in that the feed is passed across the filter membrane (tangentially) at positive pressure relative to the permeate side. A proportion of the material which is smaller than the membrane pore size passes through the membrane as permeate or filtrate; everything else is retained on the feed side of the membrane as retentate.

Suitable membranes are commercially available, for instance from Merck Millipore under the trade name Pellicon™ of from Sartorius under the tradename Hydrosart™.

The process of the present invention expediently works with membranes having a molecular weight cut-off (MWCO) of ≤5 kDA, preferably of ≤2.5 kDA, more preferably of 0.5 to 2.5 kDA, even more preferably of 1.8 to 2.2 kDA.

The tangential flow filtration takes place at a transmembrane pressure of 0.5 to 10.0 bar, more preferably of 1.0 to 4 bar, even more preferably 1.5 to 2.0 bar.

The flux, which describes the flow rate per unit area, is usually selected in the range of 5 to 50 l/h*m$^2$, preferably in the range of 9 to 15 l/h*m$^2$.

The oligonucleotide content in the acidic buffer solution is selected between 1.0 mg/l and 100.0 mg/l, preferably between 5.0 mg/l and 50.0 mg/l.

In a further embodiment of the invention the process further comprises the following steps, which come after the removal of the acid labile 5'hydroxy protecting group at the 5'-O-oligonucleotide terminus of the oligonucleotide:

a neutralization step comprising the neutralization of the resulting retentate with a base via tangential flow filtration; and a desalting step comprising the washing of the retentate obtained from the neutralization step with water or a mixture of water and a polar protic or a polar aprotic organic solvent via tangential flow filtration; and optionally a lyophilization of the retentate obtained from the desalting step.

Suitable bases for the neutralization of the retentate are aqueous inorganic bases such as aqueous alkali hydroxides like aqueous sodium hydroxide or alkaline buffers.

The subsequent washing of the filtrate can happen with water or a mixture of water and a polar protic organic solvent, selected from the primary aliphatic alcohols such as methanol, ethanol or i-propanol, preferably ethanol.

Typically, the desalting step takes place with a gradient, i.e. starting with a mixture of water and the polar protic organic solvent and ending with water.

The volume ratio water to polar protic organic solvent in the mixture is usually between 1:1 and 6:1, preferably 4:1 to 3:2.

The parameters for the tangential flow filtration during the neutralization but also for the desalting step, i.e. the transmembrane pressure, the permeate flow rate and the membrane type typically correspond with the parameters described for the previous step comprising the removal of the acid labile 5'hydroxy protecting group.

After the desalting step the retentate obtained can be subjected to a lyophilisation step or a further purification such as for the removal of residual solvent from the oligonucleotide.

In the most preferred embodiment the process is characterized by
- the removal of the acid labile 5'hydroxy protecting group at the 5'-O-oligonucleotide terminus of the oligonucleotide by way of tangential flow filtration with an acidic buffer solution
- a neutralization step comprising the neutralization of the resulting retentate with a base via tangential flow filtration; and
- a desalting step comprising the washing of the retentate obtained from the neutralization step with water or a mixture of water and a polar protic or a polar aprotic organic solvent via tangential flow filtration; and
- optionally a lyophilization of the retentate obtained from the desalting step.

The deprotection step, the neutralization step and the desalting step are sequential tangential flow filtration steps, can be automated and carried out by the same software-controlled apparatus, without any human operator intervention.

As outlined above the oligonucleotide after its formation on the resin is cleaved off from the resin usually with concentrated aqueous ammonia. The protecting groups on the phosphate and the nucleotide base are also removed within this cleavage procedure with the exception of the acid labile 5'hydroxy protecting group at the 5'-O-oligonucleotide terminus of the oligonucleotide.

In a preferred embodiment the process further comprises the following step which comes previous to the removal of the acid labile 5'hydroxy protecting group at the 5'-O-oligonucleotide terminus of the oligonucleotide. This previous step aims at removing shorter length (non-5'-protected) truncates of the desired oligonucleotide.
- Reversed Phase high performance liquid chromatography or anion exchange chromatography of the crude oligonucleotide obtained after cleavage form the resin and phosphate deproetction.

The anion-exchange chromatography is based on the competitive interaction of charged ions of the sample solution with the buffer medium employed. It can be carried out with conventional, commercially available anion-exchange resins, preferably those with trimethylammonium-functionalization. These phase materials can be obtained for example from GE Healthcare, Tosoh Bioscience, Bio-Rad or Merck. Particular good results have been achieved with the anion-exchange resin TSKgel Super Q-5PW (QAE), available from Tosoh Bioscience.

The reversed-phase chromatography can be carried out with traditional, commercially available phase materials, typically C8 or C18 phase materials, such as a modified silica gel sorbents as stationary phase and suitable organic solvents such as acetonitrile and, if applicable, a buffer. Suitable modified silica gel type phase materials can be selected from Kromasil™C18, Kromasil™C8, YMC Triart C18 and YMC Triart C8.

By way of illustration the oligonucleotide can be selected from the group consisting of:

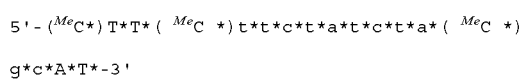

wherein * stands for phosphorthioate bridges; A, G, T and $^{Me}$C (5-methyl cytosine) are LNA nucleoside monomers and a, t, c, g are DNA nucleoside monomers.

The compounds disclosed herein have the following nucleobase sequences
SEQ ID No. 1: cnctctatctacgcat'

EXAMPLES

Abbreviations:
ACN=acetonitrile
Ac$_2$O=acetic acid anhydride
CV=column volume
DAC=dichloroacetic acid
DCM=dichloromethane
DMT=4,4'-dimethoxytrityl
EtOH=ethanol
NaOAc=sodium acetate
NMI=N-methyl imidazole?

Example 1 a. Synthesis of 5'-($^{Me}$C*)T*T*($^{Me}$C*) t*t*c*t*a*t*c*t*a*($^{Me}$C*)g*c*A*T*-3'

The title compound was synthesized as "DMT-on" using an ÄKTA oligopilot-100 on a 1.9 mmol scale. Synthesis parameters are given in Table 1.

TABLE 1

Synthesis parameters for ÄKTA OP-100.

| Process Step | Parameter | Set Point |
|---|---|---|
| Coupling | Concentration of LNA-C amidite | 0.2M DCM/ACN 1:1 |
| | Concentration of other amidites | 0.2M ACN |
| | Eq. amidite to support | 1.5 eq |
| | Activator | BTT |
| | Conc. activator | 0.3M in ACN |
| | % Volume of activator solution | 65% |
| | Recycle time | 10.0 min (LNA) 7.5 min (DNA) |
| | Coupling wash flow rate | 24 mL/min |
| | Coupling wash volume | 12 mL |
| Thiolation | Reagent | Xanthan hydride |
| | Concentration | 0.1M in ACN/pyridine 1:1 |
| | Volume | 2 CV |
| | Recycle or flow through | Flow through |
| | Push flow rate | 17 mL/min |
| | Push volume | 1 CV |
| | ACN wash volume | 8.5 mL |
| Synthesis Column | Scale | 1.9 mmol |
| | Support | NittoPhase UnyLinker |
| | Weight of support | 4.6 g |
| | Support loading | 0.417 mmol/g |
| | Column Diameter | 44 mm |
| | Column Volume | 48 mL |
| Detrytilation | Reagent | 3% DCA |
| | Control mode | UV |
| | UV monitoring | 350 nm |
| | Detrytilation flow rate | 400 cm/h |
| | ACN wash | 96 mL |
| | ACN wash flow rate | 7 bar |
| | ACN wash | 96 mL |
| | ACN wash flow rate | 15 bar |
| Capping | Reagents | Cap A: 20% v/v NMI in ACN |
| | | Cap B: 30% v/v lutidine, 20% v/v Ac$_2$O in ACN |

TABLE 1-continued

Synthesis parameters for ÄKTA OP-100.

| Process Step | Parameter | Set Point |
|---|---|---|
| | Charge Volume | 96 mL (1:1 Cap A/Cap B) |
| | Charge flow rate | 120 mL/min |
| | Contact time | 0.8 min |
| | ACN push/wash volume | 216 mL |
| | ACN push/wash volume | 144 mL |
| Post Synthesis Wash | Wash solvent | ACN |
| | Wash volume | 288 mL |
| | Wash time | 3 minutes |
| Post Synthesis DEA wash (on column and on synthesizer) | Solution | 20% v/v in ACN |
| | Flow through or recycle | Flow through |
| | Volume | 235 mL |
| | Contact time | 30 minutes |
| Final Column Wash | Wash solvent | ACN |
| | Wash volume | 288 mL |
| | Wash time | 3 minutes | b. Cleavage from Solid Support and RP-HPLC Purification

The crude material was cleaved from the resin and deprotected by dissolving the dried resin in aqueous 30% ammonia solution (190 mL) and stirring at 65° C. for 5 h. The solid support was filtered off and the aqueous solution was concentrated by rotary evaporation to approximately 60 mL. The solution was further diluted with $H_2O$ to a final volume of 100 mL and solid $Na_2CO_3$ was added to obtain a 50 mM $Na_2CO_3$ solution (124 mg/mL crude oligo content). A portion of crude material (80 mL) was purified by RP-HPLC according to the parameter in Table 2.

TABLE 2

RP-HPLC purification parameters.

| Process Parameter | Set Point | | |
|---|---|---|---|
| Column type | YMC Triart C18 preparative | | |
| Column temperature | 23° C. | | |
| Feed solution composition | 124 mg/mL total oligo content in 50 mM $Na_2CO_3$ | | |
| Total Volume of feed solution | 80 mL | | |
| Volume per Injection | 4 mL | | |
| Elution Solvent A | 50 mM $Na_2CO_3$ | | |
| Elution Solvent B | ACN | | |
| Gradient | Time (min) | A (%) | B (%) |
| | 0 | 95 | 5 |
| | 3 | 85 | 15 |
| | 15 | 75 | 25 |
| | 17 | 75 | 25 |
| | 17.10 | 10 | 90 |
| | 20 | 10 | 90 |
| | 20.10 | 95 | 5 |
| | 26 | 95 | 5 |
| Fraction Size | 48 mL | | | c. DMT Deprotetction, Desalting and Concentration by Tangential Flow Filtration The fractions from RP purification were pooled to obtain 2.5 L (2 mg/mL of oligo) and were diluted with $H_2O$ to a final volume of 4.2 L. The material was treated on an ÄKTA crossflow machine equipped with two 2 kD cut off Hydrosart Sartocon cassettes (0.1 m$^2$) in order to trigger DMT deproetction, concentration and tangential flow filtration. The program parameters are described in detail in Table 3.

TABLE 3

Detailed parameters for the ÄKTA crossflow program.

| Process Step | Details of Step |
|---|---|
| 1. Concentration | 4.2 L concentrated to 0.2 L |
| 2. EtOH dilution | Dilute with 80 mL EtOH |
| 3. Deprotetction | Tangential flow filtration with 5.5 L of deprotection buffer [NaOAc 100 mM, acidified to pH 3 with HCl + 40% EtOH] |
| | Oligonucleotide content: 18 mg/l |
| | Transmembrane pressure: 1.5 bar |
| | Permeate flow: 20 ml/min |
| | Flux: 12 L/h*m$^2$ |
| | Total time: 4.8 hours |
| 4. Neutralization | Tangential flow filtration with 130 mL of 0.1M NaOH |
| | Transmembrane pressure: 1.5 bar |
| | Permeate flow: 20 ml/min. |
| | Flux: 12 L/h*m$^2$ |
| | Total time: 6 minutes |
| 5. Desalting | Tangential flow filtration with 3.0 L of $H_2O$/EtOH (4:1) |
| | Total time: 2.4 hours ($H_2O$/EtOH 4/1) |
| | Transmembrane pressure: 1.5 bar |
| | Permeate flow 20 mL/min. |

The solution obtained after rinsing was lyophilized to obtain 4.00 g of the title product (overall yield based on synthesis scale 42%, UV purity 88%).

The invention claimed is:

1. A process for the purification of oligonucleotides comprising
removing an acid labile 5'hydroxy protecting group at the 5'-O-oligonucleotide terminus of the oligonucleotide by way of tangential flow filtration with an acidic buffer solution.

2. The process of claim 1, wherein the acid labile 5'hydroxy protecting group is selected from 4,4'-dimethoxytrityl, 4-methoxytrityl, trityl, 9-phenyl-xanthen-9-, 9-(p-tolyl)-xanthen-9-yl or from tert-butyldimethylsilyl.

3. The process of claim 1, wherein the acidic buffer solution has a pH in the range of 2 to 6.

4. The process of claim 1, wherein the acidic buffer is an aqueous solution of a weak acid and its conjugate base which is acidified with a protonic acid to bring the pH in the desired range.

5. The process of claim 4, wherein the acidic buffer is an acetate buffer and the protonic acid is hydrochloric acid.

6. The process of claim 1, wherein the acidic buffer solution in addition contains a polar protic or a polar aprotic organic solvent.

7. The process of claim 1, wherein the tangential flow filtration takes place at a transmembrane pressure of 0.5 to 10.0 bar.

8. The process of claim 1, wherein the tangential flow filtration takes place at a flux rate between 5 and 50 l/h*m$^2$.

9. The process of claim 1, wherein the tangential flow filtration takes place with membranes having a molecular weight cut-off (MWCO) of ≤5 kDA.

10. The process of claim 1, wherein the oligonucleotide content in the acidic buffer solution is selected between 1.0 mg/l and 100.0 mg/l.

11. The process of claim 1, wherein the process further comprises the following steps, which come after the removal of the acid labile 5'hydroxy protecting group at the 5'-O-oligonucleotide terminus of the oligonucleotide
 a. a neutralization step comprising the neutralization of the resulting retentate with a base via tangential flow filtration; and
 b. a desalting step comprising the washing of the retentate obtained from the neutralization with water or a mixture of water and a polar protic or a polar aprotic organic solvent step via tangential flow filtration; and
 c. optionally a lyophilization of the retentate obtained from the desalting step.

12. The process of claim 1, wherein the process further comprises the following step which come previous to the removal of the acid labile 5'hydroxy protecting group at the 5'-O-oligonucleotide terminus of the oligonucleotide
 a. Reversed Phase high performance liquid chromatography or anion exchange chromatography of the crude oligonucleotide obtained after cleavage from the resin and phosphate deprotection.

13. Process of claim 1, wherein the oligonucleotide consists of optionally modified DNA, RNA or LNA nucleoside monomers or combinations thereof and is 10 to 40 nucleotides in length.

* * * * *

SEQUENCE LISTING

<160> NUMBER OF SEQ ID NOS: 1

<210> SEQ ID NO 1
<211> LENGTH: 17
<212> TYPE: DNA
<213> ORGANISM: Artificial Sequence
<220> FEATURE:
<223> OTHER INFORMATION: Artificial oligonucleotide sequence

<400> SEQUENCE: 1
cttctctatc tacgcat                                                    17